US008916030B2

(12) United States Patent
He et al.

(10) Patent No.: US 8,916,030 B2
(45) Date of Patent: Dec. 23, 2014

(54) ETHYLENE CRACKING FURNACE (75) Inventors: Xiou He, Beijing (CN); Guoqing Wang, Beijing (CN); Changli Li, Beijing (CN); Lijun Zhang, Beijing (CN); Jinke Li, Jiangsu (CN); Chen Shao, Beijing (CN); Guang Li, Beijing (CN); Yuping Guo, Beijing (CN)

(73) Assignees: China Petroleum & Chemical Corp., Beijing (CN); Nanjing Industrial Furnace Institute of Tianhua of Chemical Machinery & Automation, Nanjing (CN); Sinopac Engineering Incorporation, Beijing (CN); Beijing Research Institute of Chemical Industry, China Petroleum & Chemical Corp., Beijing (CN)

( * ) Notice: Subject to any disclaimer, the term of this patent is extended or adjusted under 35 U.S.C. 154(b) by 919 days.

(21) Appl. No.: 13/124,590

(22) PCT Filed: Oct. 15, 2009

(86) PCT No.: PCT/CN2009/001145
§ 371 (c)(1),
(2), (4) Date: Oct. 11, 2011

(87) PCT Pub. No.: WO2010/043116
PCT Pub. Date: Apr. 22, 2010

(65) Prior Publication Data
US 2012/0020852 A1 Jan. 26, 2012

(30) Foreign Application Priority Data
Oct. 16, 2008 (CN) .......................... 2008 1 0224277

(51) Int. Cl.
C10G 9/14 (2006.01)
B01J 8/00 (2006.01)
C07C 4/02 (2006.01)

(52) U.S. Cl.
CPC .............. *C07C 4/02* (2013.01); *C10G 2400/20* (2013.01)
USPC ........... 202/222; 202/265; 422/641; 422/645; 422/652; 422/659

(58) Field of Classification Search
USPC ........... 208/132; 202/222, 265; 422/641, 645, 422/651, 652, 659; 165/181, 182, 183, 184
See application file for complete search history.

(56) References Cited

U.S. PATENT DOCUMENTS

| | | | | |
|---|---|---|---|---|
| 5,271,809 A * | 12/1993 | Holzhausen | ................... | 196/110 |
| 6,528,027 B1 * | 3/2003 | Brewer et al. | ................. | 422/200 |
| 7,004,085 B2 * | 2/2006 | Platvoet et al. | ............... | 110/203 |
| 7,128,139 B2 * | 10/2006 | Oballa et al. | ................... | 165/181 |
| 7,799,963 B2 * | 9/2010 | Inui et al. | ....................... | 585/652 |
| 7,963,318 B2 * | 6/2011 | Wolpert et al. | ............... | 165/184 |
| 7,964,091 B2 * | 6/2011 | Barendregt et al. | ........... | 208/132 |
| 8,354,084 B2 * | 1/2013 | Tallis | ............................ | 422/659 |
| 8,585,890 B2 * | 11/2013 | Wang et al. | ................... | 208/132 |
| 8,747,765 B2 * | 6/2014 | Spicer et al. | ................... | 422/198 |
| 8,790,602 B2 * | 7/2014 | Petela et al. | .................. | 422/659 |
| 2003/0070962 A1 * | 4/2003 | Zeng et al. | .................... | 208/106 |
| 2011/0257455 A1 * | 10/2011 | Spicer et al. | ................. | 585/648 |

FOREIGN PATENT DOCUMENTS

| | | | |
|---|---|---|---|
| CA | 2 290 540 A1 | 12/1998 | |
| CN | 1067669 A | 1/1993 | |
| CN | 1259981 A1 | 7/2000 | |
| CN | 101062881 A | 10/2007 | |
| CN | 101062884 A | 10/2007 | |
| CN | 201276507 Y | 7/2009 | |
| EP | 1146105 A2 | 10/2001 | |

OTHER PUBLICATIONS

English abstract of CN 101062881A from the espacenet database.
English abstract of CN 101062884A from the espacenet database.
English abstract of CN 1067669A from the espacenet database.
English abstract of CN 201276507Y from the espacenet database.
English abstract of EP 1146105A2 from the espacenet database.

International Search Report mailed Jan. 28, 2010 for PCT/CN2009/001145.

* cited by examiner

*Primary Examiner* — Nina Bhat
(74) *Attorney, Agent, or Firm* — Finnegan, Henderson, Farabow, Garrett & Dunner LLP (57) ABSTRACT

An ethylene cracking furnace comprising a high pressure steam drum (1), a convection section (2), a radiant section (3), multiple groups of radiant coils (4) arranged vertically in the firebox of radiant section, burners (5) and transfer line exchangers (6), each radiant coil comprising a first-pass tube (7), a second-pass tube (8) and a connection member (9); feedstocks being introduced into an inlet end of the first-pass tube and outflow from an outlet end of the second-pass tube, said first-pass tube (7) and said second-pass tube (8) are non-split coils, and the centerlines of the respective radiant tubes (7, 8) are within a common plane; said connection member (9) is a tridimensional structural member comprising an inlet bending tube (10), a return bending tube (11) and an outlet bending tube (12); said inlet bending tubes (10) and said outlet bending tubes (12) are arranged at two sides of the plane containing the centerlines of said first-pass tubes (7) and said second-pass tubes (8), respectively; the projections of the respective connection members (9) in a side view are the same curve line that is symmetrical, continuous and closed; the inner diameters of said radiant coils (7, 8) is varied at least once along the length of the tubes.

10 Claims, 8 Drawing Sheets

ETHYLENE CRACKING FURNACE

TECHNICAL FIELD

The present invention generally relates to the field of petrochemical industry, and specifically relates to a furnace tube structure of an ethylene cracking furnace being used in petrochemical industry.

BACKGROUND OF THE INVENTION

A cracking furnace is a critical equipment of an ethylene plant. The design of the radiant coils of the ethylene cracking furnace is the critical factor for determining the cracking selectivity, increasing the olefin yields in the pyrolysis products and the flexibility for different feedstocks. Improving the structure and arrangement of the radiant coils becomes the most important part for the technological development of tubular cracking furnace. In the recent decades, several arrangements with different structures, including single-row split diameter-varying tube type, mixed-rows split diameter-varying tube type, non-split diameter-varying tube type, single-pass even-diameter tube type, etc., have been presented.

The arrangement manner of the furnace tubes has been developed from the original single-row manner to the double-row manner. With regard to the single-row manner, it would need more floor space for the same manufacturing capacity, but its advantages are that: the temperature distribution circumferentially around the furnace tubes is uniform and there is little obscur phenomenon; with regard to the double-row manner, it can substantively reduce the floor space of the cracking furnace, however, the obscur phenomenon is very serious and thus the temperature distribution circumferentially around the furnace tubes is negatively affected.

Lummus Crest Inc. (US) discloses a furnace arrangement in China Patent CN1067669 having six first-pass tubes and one second-pass tube, the first tubes being connected at their lower ends via a manifold conduit to the second-pass tube. This kind of structure, as having six first-pass tubes and one second-pass tube, when the furnace tubes are subjected to heat and thus expand, the second-pass tube firstly expands downwardly, and the first-pass tubes move downwardly due to the traction of the second-pass tube, where the first-pass tubes farer from the second-pass tube are subjected to less force, and the first-pass tubes nearer to the second-pass tube are subjected to more force; In addition, due to that the upper and lower manifold conduits are connected rigidly, the expansion difference between the second-pass tube and the first-pass tubes can only be adjusted by the balance system arranged at the inlet of the first-pass tubes, and thus the results are that: when the first-pass tubes cannot move together with the second-pass tube, the furnace tubes will be bent Exxon Chemical Patents Inc. (US) discloses an arrangement in Patent CN1259981, and meanwhile discloses another arrangement in U.S. Pat. No. 6,528,027. The common drawback of the two different arrangements of the radiant tube are that: as the lower part a first-pass tube inclines outwardly but the second-pass tube do not incline in a reverse direction, meanwhile the adjacent first-pass tube inclines toward the other side, the results are that, when the radiant tubes are subjected to the heating, the overall radiant coils cannot be kept in a single-row, and will naturally present a two-row so as to eliminate stresses. The result is that, the heating of the radiant tubes are not uniform and thus there have the temperature difference between the two sides of the radiant tube walls, the temperature of the side adjacent to burners is high and the temperature of the opposite side is low, thus the furnace tubes will bend toward the burners.

Patent EP1146105 discloses a cracking furnace with such a kind of tube arrangement: two-passes radiant coils are vertically disposed in the firebox of the radiant section, the linear tube portions of the first-pass tubes and the second-pass tubes are arranged in a common plane, each of the first-pass straight tubes and the second-pass tubes is connected to a curved tube via a "S" shaped tube, respectively, the "S" shaped tubes of the first-pass tubes and the second-pass tubes are parallel, respectively, the shape of connecting curved tube may be semi-circle, semi-ellipse or semi-oviform, the angle formed by the respective curved tubes with respect to the plane containing the linear tube portions are the same. This kind of tube arrangement overcomes the drawbacks of the aforementioned radiant tube structure. However, as the 2-1 type furnace tube has a "Y" shaped tube at the lower portion of "two-tube section" of the first-pass tube, tube bending would still exist due to that the two tubes connected to the "Y" shaped tube are different with regard to the expansion due to the heating of the radiant tubes.

When reviewing the aforementioned prior art, it can be seen that none of the various conventional radiant tube arrangements can avoid tube deformation or bending and displacement. Further, this kind of deformation or bending will make that the heating of the radiant tube is not uniform, and thus the radiant tubes will be further deformed and displaced. The heat absorptivity is thus limited and the lifespan of the radiant tubes of cracking furnace is shortened.

SUMMARY OF THE INVENTION

An object of the present invention is to solve the difficult problems of the prior art by providing an ethylene cracking furnace having two-pass radiant coils that can ensure uniform heating, fine mechanical performance and extended lifespan.

The object is realized by the following technical solutions.

An ethylene cracking furnace comprising a high pressure steam drum, a convection section, a radiant section, multiple groups of radiant coils arranged vertically in the firebox of the radiant section, burners and transfer line exchangers, each radiant coil comprising a first-pass tube, a second-pass tube and a connection member for connecting the first-pass tube and the second-pass tube; feedstocks being introduced into an inlet end of the first-pass tube and outflow from an outlet end of the second-pass tube; said first-pass tube and said second-pass tube are non-split radiant tubes, and the centerlines of the respective radiant tubes are within a common plane; said connection member is a tridimensional structural member comprising an inlet bending tube, a return bending tube and an outlet bending tube; each first-pass tube is connected to an end of an inlet bending tube at the bottom end of the first-pass tube distal to the inlet end thereof, another end of the inlet bending tube is connected to an end of a return bending tube, another end of the return bending tube is connected to an end of an outlet bending tube, and another end of the outlet bending tube is connected to the bottom end of a second-pass tube that is distal to the outlet end thereof; said inlet bending tubes and said outlet bending tubes are arranged at two sides of the plane containing the centerlines of said first-pass tubes and said second-pass tubes, respectively; a plane formed by the centerlines of a group of inlet bending tubes intersects with a plane formed by the centerlines of a group of outlet bending tubes (in a side view), the intersecting line is within the plane containing the centerlines of said first-pass tubes and said second-pass tubes, and said two planes formed by the centerlines of the inlet bending tubes and the outlet bending tubes are symmetrical with respect to the plane containing the centerlines of said first-pass tubes and said second-pass tubes; the return bending tubes connecting the group of inlet bending tubes and the group of outlet bending tubes are parallel to each other, and their projections in a top view are straight lines with the same length; the projections of the respective connection members in a side view are the same curve line that is symmetrical, continuous and closed, and For satisfying the requirements of lowering temperature and reducing pressure drop during cracking process while keeping the heat absorptivity unchanged, the radiant coils can be arranged in a diameter-varying manner. For different requirements, the diameter-varying arrangement can be realized with many alternatives (including but not limited to the following listed alternatives), wherein the length of the first-pass tubes and the second-pass tubes are the same in each alternative:

(1) the inner diameter of said first-pass tube equals to the inner diameter of said connection member, the inner diameter of said second-pass tube differs from the inner diameter of said first-pass tube and said connection member, the inner diameter of said second-pass tube is larger than inner diameter of said first-pass tube and said connection member, this alternative can be referred to as "once diameter-varying";

(2) the inner diameter of said first-pass tube equals to the inner diameter of said connection member, the inner diameter of the lower portion of said second-pass tube equals to the inner diameter of said first-pass tube and said connection member, the inner diameter of the upper portion of said second-pass tube is larger than the inner diameter of the lower portion thereof, this alternative can be referred to as "twice diameter-varying";

(3) the inner diameter of said first-pass tube is even, the inner diameter of said connection member is larger than the inner diameter of said first-pass tube, the inner diameter of said second-pass tube equals to the inner diameter of said connection member;

(4) the inner diameter of said first-pass tube is even, the inner diameter of said connection member is larger than the inner diameter of said first-pass tube, the inner diameter of the lower portion of said second-pass tube equals to the inner diameter of said connection member, the inner diameter of the upper portion of said second-pass tube is larger than the inner diameter of the lower portion thereof, this alternative can be referred to as "triple diameter-varying";

(5) the inner diameter of said first-pass tube is even, the inner diameter of said connection member is larger than the inner diameter of said first-pass tube, the inner diameter of the lower portion of said second-pass tube is larger than the inner diameter of said connection member, the inner diameter of the upper portion of said second-pass tube is larger than the inner diameter of the lower portion thereof, this alternative can be referred to as "quartic diameter-varying"; and (6) the inner diameter of said first-pass tube is variational: the inner diameter of the lower portion of said first-pass tube is larger than the inner diameter of the upper portion thereof.

With the abovementioned diameter-varying arrangements, the cross-section area of the radiant coil increases as the cracking process advances, thus the pressure drop along the tube length is decreased (the partial pressures of hydrocarbons are decreased) and thus the requirements of the cracking reaction are better satisfied, resulting in a high cracking performance. For the same yield of the cracking products, the cracking temperature can be lowered; while for the same cracking temperature, the yield of the ethylene products can be effectively improved.

In accordance with a preferred embodiment of the present invention, in each group of radiant coils, the respective first-pass tubes are parallel to each other, the respective second-pass tubes are parallel to each other, and the first-pass tubes and the second-pass tubes are parallel to each other; the projection of the plane containing the centerlines of said first-pass tubes and said second-pass tubes in a top view is a straight line; said respective inlet bending tubes are parallel to each other with their projections in a top view forming the same inlet angle with respect to said straight line; said respective outlet bending tubes are parallel to each other with their projections in a top view forming the same outlet angle with respect to said straight line; said inlet angle equals to said outlet angle.

In accordance with a preferred embodiment of the present invention, in each group of radiant coils, the respective first-pass tubes are parallel to each other, the respective second-pass tubes are parallel to each other, and the first-pass tubes and the second-pass tubes are parallel to each other; the projection of the plane containing the centerlines of said first-pass tubes and said second-pass tubes in a top view is a straight line; said respective inlet bending tubes are not parallel to each other with their projections in a top view forming different inlet angles with respect to said straight line; said respective outlet bending tubes are not parallel to each other with their projections in a top view forming different outlet angles with respect to said straight line; but for each radiant tube, said inlet angle equals to said outlet angle.

In accordance with a preferred embodiment of the present invention, said radiant coils may comprise at least one tube section having a twisted baffle therein, said twisted baffle extends inside the tube section along the axis thereof to form two helical passages at the opposite sides of said twisted baffle, said twisted baffle being integrally formed with said tube section.

As having twisted baffles provided within the radiant coils of the present invention, when the in-process materials pass through the surface of said twisted baffle inside the tube section, said twisted baffle directs the in-process materials away from the center of the tube section, flowing forward helically other than straight forward, so that the in-process materials passing through inside the tube section flow laterally while going forward, so as to strongly spray onto the inner surface of the tube section. In this way, the thickness of the peripheral laminar-flow layer (which normally has high heat resistance, especially when having large thickness) on the inner surface of the tube section is substantively decreased, and therefore the heat transfer efficiency is improved. The improved heat transfer efficiency, in turn, lowers the temperature of the inner wall of the radiant coils and thus the coking tendency is restrained, and this will further improve the heat transfer efficiency.

In accordance with a preferred embodiment of the present invention, the twisted angle of said twisted baffle is between 100-360°, the axial length of said tube section with every twisted angle 180° of the twisted baffle is a pitch, the ratio of said pitch to the inner diameter of said tube section is in the range of from 2 to 3; the thickness of said twisted baffle substantially corresponds to that of the wall of said tube section; in each cross-section of said tube section, the transition zone from the surface of said twisted baffle to the surface of said tube section, and vice versa, is in the shape of a concave circular arc.

In accordance with a preferred embodiment of the present invention, said radiant coils comprise multiple tube sections each having a twisted baffle therein, the multiple tube sections are arranged in at least a predetermined length of said radiant coils spaced apart with each other, the distance between two adjacent tube sections is at least five pitches. This kind of arrangement makes that: the total length of all said tube sections with the twisted baffle(s) is only a small part of the entire length of the radiant coils. Therefore, the resistance to the flowing in-process materials would not be increased substantially, so that the in-process materials can go forward in a helical motion state so as to improve the heat transfer efficiency, while the flowing speed of the in-processing flow would not decrease substantially.

With the help of said twisted baffle inside said tube section, the in-processing materials are directed laterally away from the center of the tube section, so as to strongly spray onto the inner surface of the tube section. In this way, the thickness of the peripheral laminar-flow layer (which normally has high heat resistance, especially when having large thickness) on the inner surface of the tube section is substantively decreased. Therefore, the resistance of the tube wall to the in-processing materials is decreased, thus the advance speed of the in-processing materials can be properly increased.

As the temperature of the inner walls of the radiant coils of the cracking furnace is lowered, the lifespan of the radiant coils of the cracking furnace is extended.

With the same reasons, by means of arranging said tube section(s) with the twisted baffle(s) in the tubular cracking furnace, the heat transfer efficiency can be improved with a lower cost, and larger amount of flowing in-processing materials can go through the furnace.

In accordance with a preferred embodiment of the present invention, the projection shape of said return bending tube in a side view is camber, semi-circular, semi-ellipse or parabola.

In accordance with a preferred embodiment of the present invention, said group of radiant coils may comprise at least two radiant coils, and all of the first-pass tubes and all of the second-pass tubes in each group of radiant coils are collectively arranged, respectively.

In accordance with a preferred embodiment of the present invention, the second-pass tubes of two groups of radiant coils are adjacently arranged so as to form a module; a plurality of said modules are arranged within the radiation section of the cracking furnace, and the centerlines of the first-pass tubes and the second-pass tubes of each of the groups are within the same plane.

In accordance with a preferred embodiment of the present invention, the radiation section of the cracking furnace is arranged with multiple groups of radiant tubes, the first-pass tubes of one group of radiant tubes are arranged adjacent to the second-pass tubes of another group of radiant tubes, and the centerlines of the first-pass tubes and the second-pass tubes of each of the groups are within the same plane.

In the abovementioned arrangements, due to that the projections of the respective connection members in a side view are the same curve line that is symmetrical, continuous and closed, when subjected to heat, the deformation of the connection members is also symmetrical. Therefore, it can ensure that the heating is uniform, and the single-row arrangement can be kept unchanged. Specifically, the furnace tubes of the two passes are within the same plane, the connection members of the tubes of the two passes are arranged at the two sides of said plane, the gravity center of the tubes is within the plane. Meanwhile, the first-pass tubes and the second-pass tubes are arranged together in group, respectively. When the second-pass tubes expand downwardly, both the connection members and the first-pass tubes move regularly in the same direction, thus when operating in a heating state, tube bending and movement direction differentiation (due to the gravity center of the tubes are not within the plane of the tubes) can be avoided, and thus further ensuring that the first-pass furnace tubes and the second-pass furnace tubes are within the center plane of the furnace chamber, and therefore the object of avoiding uneven heating is realized. Therefore, furnaces having such kind of arrangement of furnace tubes have advantages of long lifespan and good mechanical properties, etc.

In each group of radiant coils, the respective first-pass tubes are parallel to each other, the respective second-pass tubes are parallel to each other, and the first-pass tubes and the second-pass tubes are parallel to each other; the projection of the plane containing the centerlines of said first-pass tubes and said second-pass tubes in a top view is a straight line. However, the inlet bending tubes and the outlet bending tubes can be arranged in several manners. One manner is that: said respective inlet bending tubes are parallel to each other with their projections in a top view forming the same inlet angle with respect to said straight line; said respective outlet bending tubes are parallel to each other with their projections in a top view forming the same outlet angle with respect to said straight line; said inlet angle equals to said outlet angle. Another manner is that: said respective inlet bending tubes are not parallel to each other with their projections in a top view forming different inlet angles with respect to said straight line; said respective outlet bending tubes are not parallel to each other with their projections in a top view forming different outlet angles with respect to said straight line; but for each radiant tube, said inlet angle equals to said outlet angle.

Based on different requirements, said group of radiant coils may comprise two or more radiant coils, and all of the first-pass tubes and all of the second-pass tubes in each group of radiant coils are collectively arranged, respectively. The radiation section of the cracking furnace is arranged with multiple groups of radiant tubes and the arrangement can be in several manners, one manner is that: the second-pass tubes of two groups of radiant coils are adjacently arranged so as to form a module and the centerlines of the first-pass tubes and the second-pass tubes of the two groups are within the same plane; a plurality of said modules are arranged within the radiation section of the cracking furnace, and the centerlines of the first-pass tubes and the second-pass tubes of each of the groups are within the same plane. Another manner is that: the first-pass tubes of one group of radiant tubes are arranged adjacent to the second-pass tubes of another group of radiant tubes, and the centerlines of the first-pass tubes and the second-pass tubes of each of the groups are within the same plane. With such arrangement, when the arrangement of the tubes has odd number, the first-pass tubes and the second-pass tubes can be arranged alternately, and therefore the heating of the tubes in the firebox of the radiant section would be more uniform.

According to practical requirements, the twisted baffles may be integrated with the diameter-varying zones of the tubes so as to reduce cost and improve the heat transfer effect; the twisted baffles may also be arranged at non-variation zones of the tubes. The overall object is to improve the diameter-varying effect so as to improve the cracking performance, i.e., to extend the runlength and improve the olefin yields.

When implementing the invention, the number of the groups of the radiant coils relates to the capability of the furnace, and it can be determined in accordance with the design conditions of the feedstocks, the capacity of the cracking furnace, the runlength, etc.

Generally speaking, when comparing with the prior art technologies, the present invention provides the following beneficial effects:

(1) As the radiant coils of the present invention are arranged in a diameter-varying manner, especially a continuous and multiple diameter-varying manner, the cross-section of the radiant coil increases as the cracking process advances, thus the pressure drop within the tube length is decreased and thus the requirements of the cracking reaction are better satisfied, resulting in a high cracking performance. For the same yield of the cracking products, the cracking temperature can be lowered; on the other hand, for the same cracking temperature, the yield of the olefin products can be effectively improved.

(2) The tube wall temperature of the radiant tubes during practical operating is lowered. The runlength is extended and the times of increase and decrease the firebox temperature can be reduced. The furnace tubes have good mechanical performance and thus are not likely to be bent. The lifespan of the tubes can be extended for additional 2 to 3 years.

(3) As mentioned above, due to the provision of the tube section(s) with internal twisted baffle(s) in the radiant coils of the ethylene cracking furnace of the present invention, the ethylene cracking furnace of the present invention will provide better heat transfer efficiency, less coking tendency, stable and reliable operating properties, and additionally extended lifespan of the apparatus.

DETAILED DESCRIPTION OF THE PREFERRED EMBODIMENTS

The present invention will be described in detail hereinafter with reference to the accompanying drawings.

Figure 1:
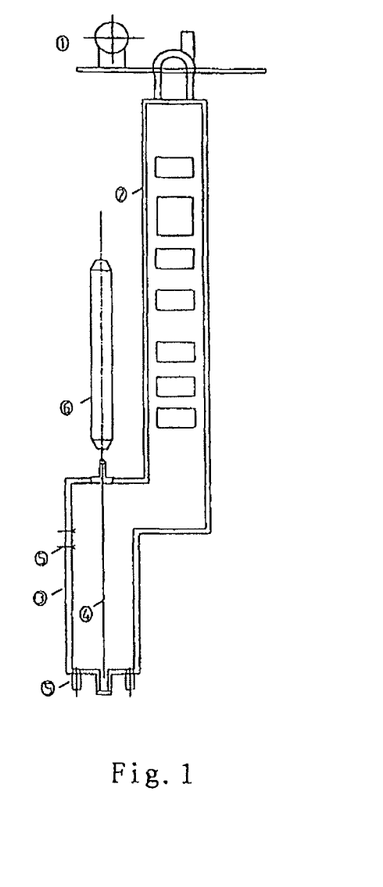
FIG. 1 is a schematic view of the cracking furnace of the present invention.

As shown in FIG. 1, the ethylene cracking furnace in accordance with the present invention comprises a high pressure steam drum 1, a convection section 2, a radiation section 3, multiple groups of radiant coils 4 arranged vertically in the radiation section, burners 5 and transfer line exchangers 6.

Figure 2:
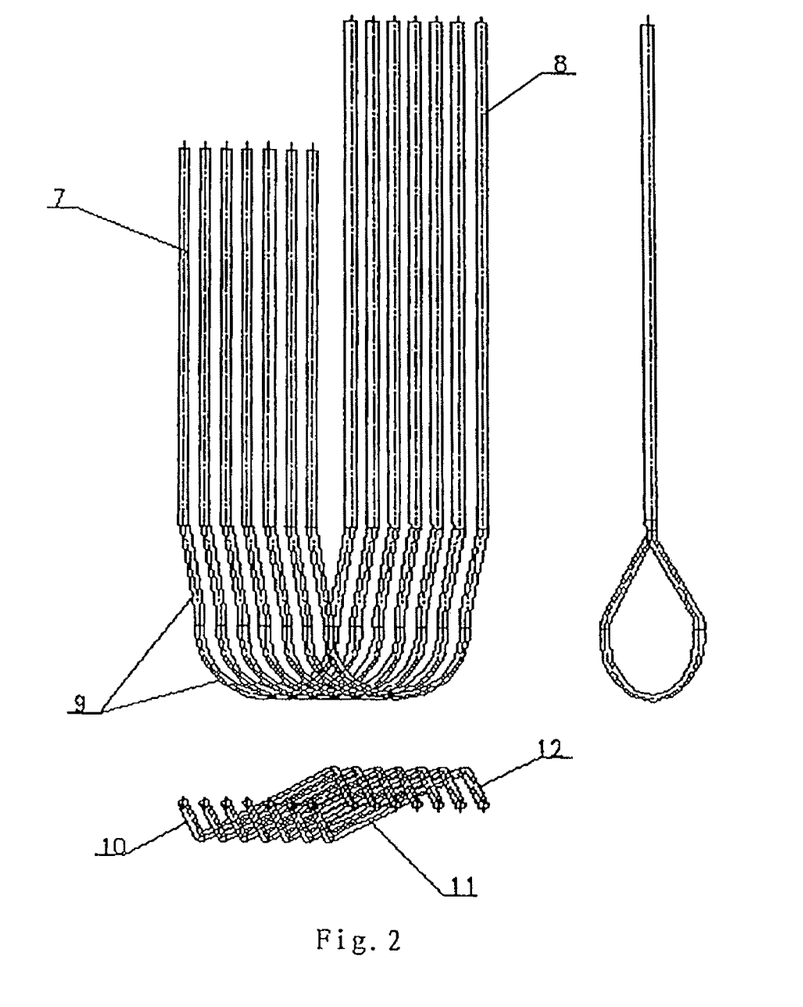
FIG. 2 is a group of schematic views (front view, side view and top view) showing a group of radiant coils in accordance with an embodiment of the present invention.

As shown in FIG. 2, each radiant coil comprises a first-pass tube 7, a second-pass tube 8 and a connection member 9 for connecting the first-pass tube and the second-pass tube; feed stocks will be introduced into an inlet end of the first-pass tube 7 and outflow from an outlet end of the second-pass tube 8.

Said first-pass tube 7 and said second-pass tube 8 are non-split furnace tubes, and the centerlines of the respective furnace tubes are within a common plane; The diameter of said first-pass tube 7, said second-pass tube 8 and said connection member 9 is varied at least once.

Said connection member 9 is a tridimensional structural member comprising an inlet bending tube 10, a return bending tube 11 and an outlet bending tube 12; each first-pass tube 7 is connected to an end of an inlet bending tube 10 at an end of the first-pass tube 7 distal to the inlet end thereof, another end of the inlet bending tube 10 is connected to an end of a return bending tube 11, another end of the return bending tube 11 is connected to an end of an outlet bending tube 12, and another end of the outlet bending tube 12 is connected to an end of a second-pass tube 8 that is distal to the outlet end thereof.

Said inlet bending tubes 10 and said outlet bending tubes 12 are arranged at two sides of the plane containing the centerlines of said first-pass tubes 7 and said second-pass tubes 8, respectively; a plane formed by the centerlines of a group of inlet bending tubes 10 intersects with a plane formed by the centerlines of a group of outlet bending tubes 12, the intersecting line is within the plane containing the centerlines of said first-pass tubes 7 and said second-pass tubes 8, and said two planes formed by the centerlines of the inlet bending tubes and the outlet bending tubes are symmetrical with respect to the plane containing the centerlines of said first-pass tubes and said second-pass tubes; the return bending tubes 11 connecting the group of inlet bending tubes 10 and the group of outlet bending tubes 12 are parallel to each other, and their projections in a top view are straight lines with the same length; the shape of the return bending tubes 11 in a side view is semi-circular. The projections of the respective connection members 9 in the side view are the same curve line that is symmetrical, continuous and closed.

In each group of radiant coils, the respective first-pass tubes 7 are parallel to each other, the respective second-pass tubes 8 are parallel to each other, and the first-pass tubes 7 and the second-pass tubes 8 are parallel to each other; the projection of the plane containing the centerlines of said first-pass tubes 7 and said second-pass tubes 8 in a top view is a straight line. However, the inlet bending tubes 10 and the outlet bending tubes 12 can be arranged in several manners:

One manner is shown in FIG. 2: said respective inlet bending tubes are parallel to each other with their projections in a top view forming the same inlet angle with respect to said straight line; said respective outlet bending tubes are parallel to each other with their projections in a top view forming the same outlet angle with respect to said straight line; said inlet angle equals to said outlet angle, preferably 70°.

Figure 3:
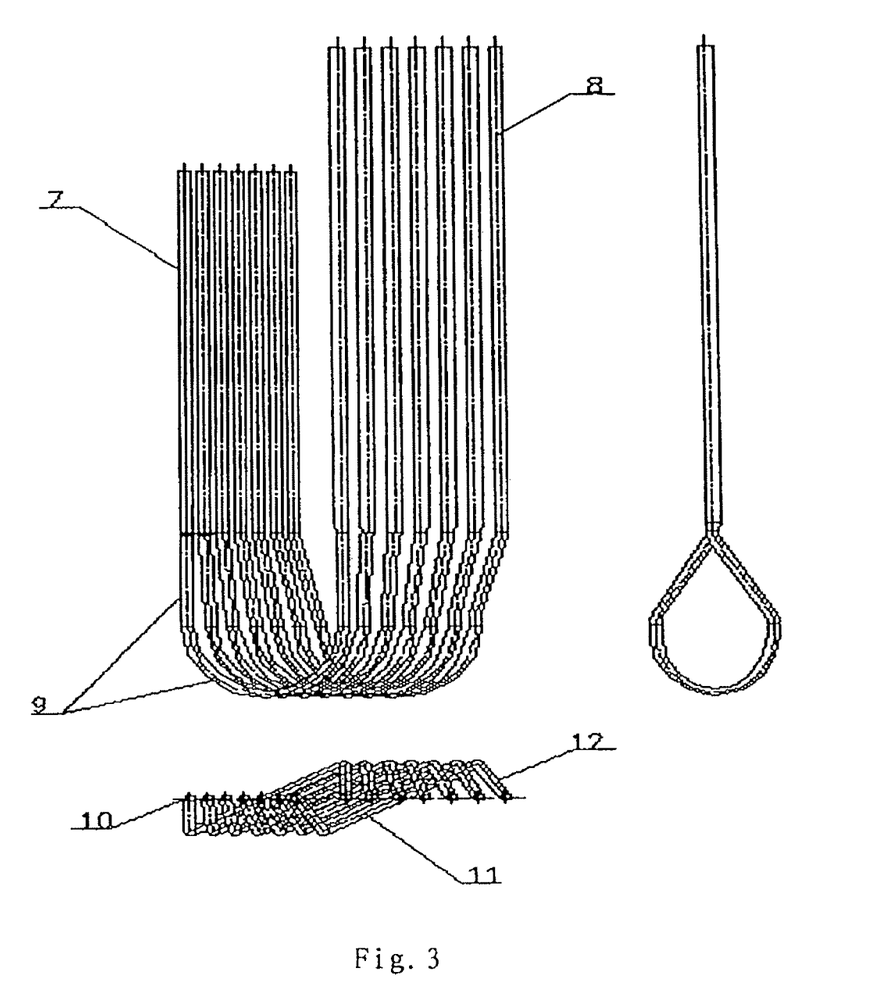
FIG. 3 is a group of schematic views (front view, side view and top view) showing a group of radiant coils in accordance with an embodiment of the present invention.

Another manner is that: said respective inlet bending tubes 10 are not parallel to each other with their projections in a top view forming different inlet angles with respect to said straight line; said respective outlet bending tubes 12 are not parallel to each other with their projections in a top view forming different outlet angles with respect to said straight line, with the angle varying in a range of 65° to 90°; but for each radiant tube, said inlet angle equals to said outlet angle.

Figure 4:
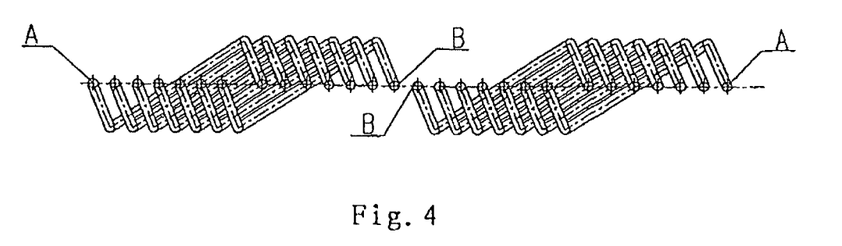
FIG. 4 is a schematic top view showing the arrangement of two groups of radiant coils in accordance with an embodiment of the present invention.
Figure 5:
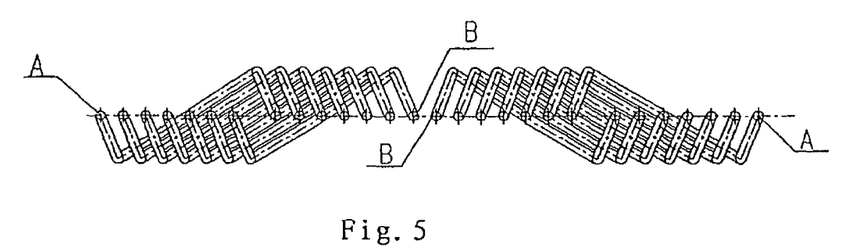
FIG. 5 is a schematic top view showing the arrangement of two groups of radiant coils in accordance with an embodiment of the present invention.
Figure 6:
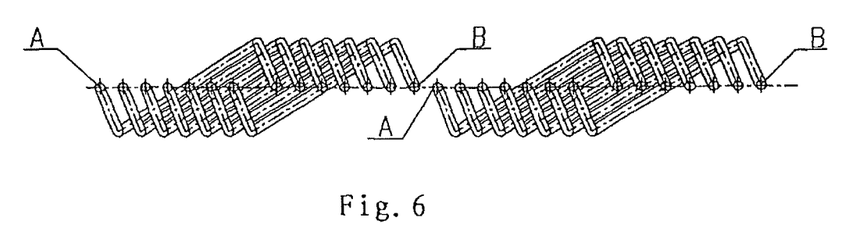
FIG. 6 is a schematic top view showing the arrangement of two groups of radiant coils in accordance with an embodiment of the present invention.

Based on different requirements, a group of radiant coils may comprise two or more radiant coils, and all of the first-pass tubes 7 and all of the second-pass tubes 8 in each group of radiant coils are collectively arranged, respectively. The radiation section of the cracking furnace is arranged with multiple groups of radiant tubes and the arrangement can be in several manners. One manner is that: the second-pass tubes of two groups of radiant coils are adjacently arranged so as to form a module and the centerlines of the first-pass tubes and the second-pass tubes of the two groups are within the same plane; the inlet bending tubes of the connection members of the first group and the inlet bending tubes of the connection members of the second group are arranged at the opposite two sides (FIG. 4) or the same side (FIG. 5); a plurality of said modules are arranged within the radiation section of the cracking furnace, and the centerlines of the first-pass tubes 7 and the second-pass tubes 8 of each of the groups are within the same plane. Another manner is shown in FIG. 6: the first-pass tubes of one group of radiant tubes are arranged adjacent to the second-pass tubes of another group of radiant tubes, and the centerlines of the first-pass tubes and the second-pass tubes of each of the groups are within the same plane.

Figure 7:
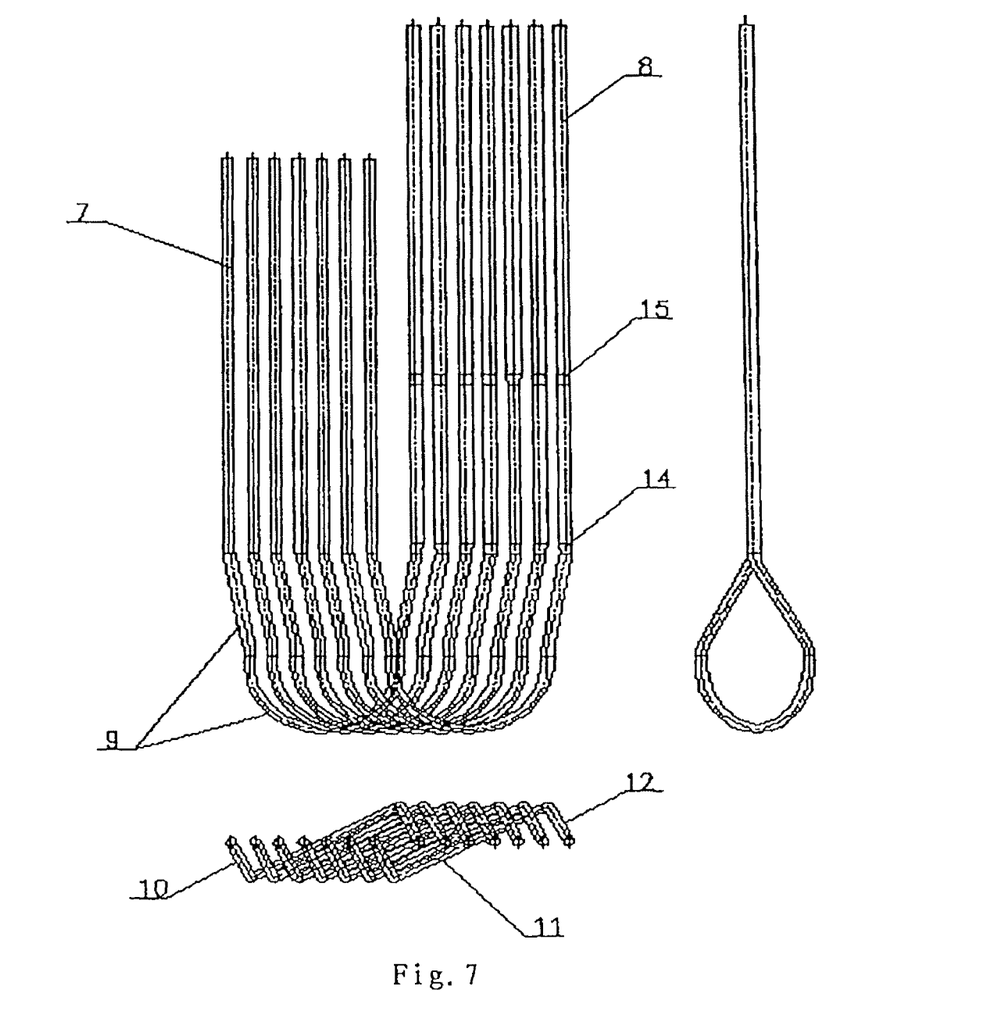
FIG. 7 is a group of schematic views showing a group of radiant coils in accordance with an embodiment of the present invention.
Figure 8:
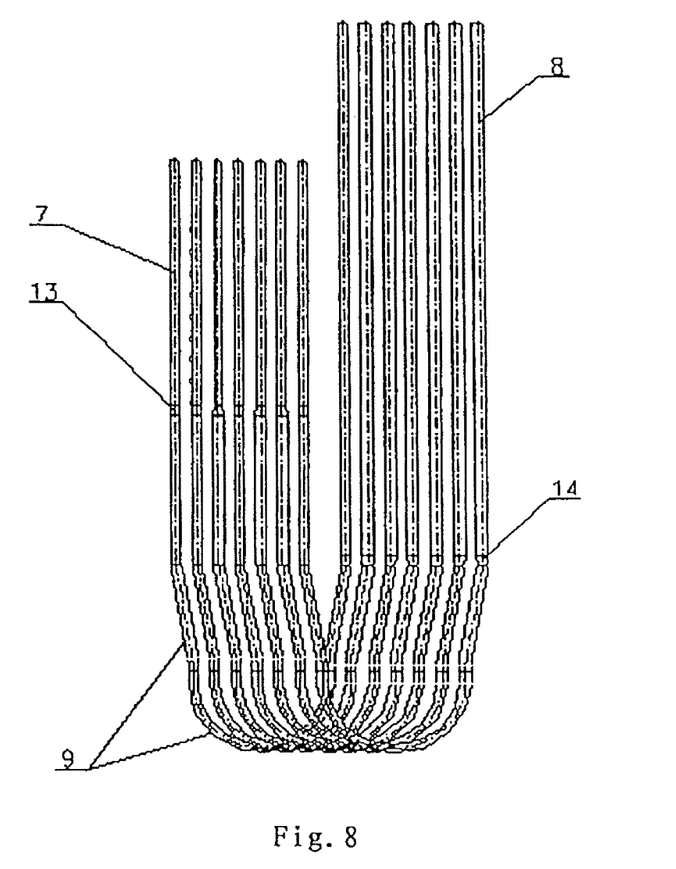
FIG. 8 is a group of schematic views showing a group of radiant coils in accordance with an embodiment of the present invention.
Figure 9:
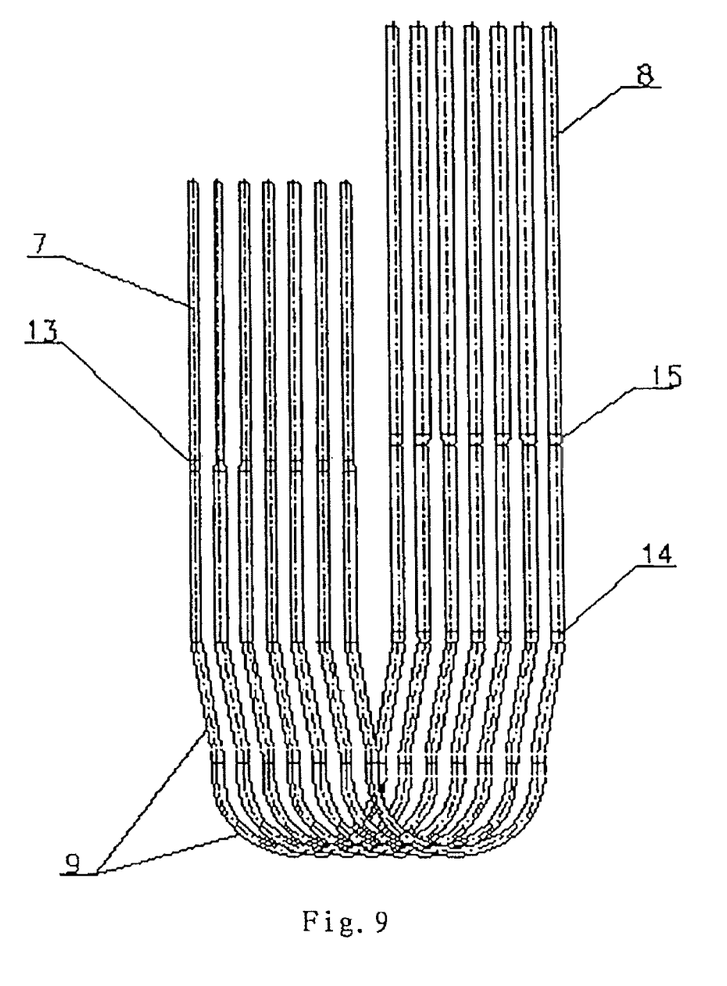
FIG. 9 is a group of schematic views showing a group of radiant coils in accordance with an embodiment of the present invention.

For satisfying the requirements of lowering temperature and reducing pressure drop during cracking process while keeping the heat absorptivity unchanged, the radiant coils can be arranged in a diameter-varying manner. For different requirements, the diameter-varying arrangement can be realized with many alternatives:

Alternative A:

the inner diameter of said first-pass tube 7 equals to the inner diameter of said connection member 9, the inner diameter of the lower portion of said second-pass tube differs from the inner diameter of said connection member 9, and the inner diameter of the upper portion of said second-pass tube 9 also differs from the inner diameter of the lower portion thereof (FIG. 7);

Alternative B:

the inner diameter of said first-pass tube 7 is varying (the inner diameter of the upper portion differs from the inner diameter of the lower portion), the inner diameter of the connection member 9 equals to that of the lower portion of the first-pass tube 7, and the inner diameter of the second-pass tube is even (unchanged) (FIG. 8);

Alternative C:

the inner diameter of said first-pass tube 7 is varying (the inner diameter of the upper portion differs from the inner diameter of the lower portion), the inner diameter of the connection member 9 equals to that of the lower portion of the first-pass tube 7, the inner diameter of the lower portion of the second-pass tube 8 differs from that of the connection member 9, and the inner diameter of the upper portion of the second-pass tube 8 differs from that of the lower portion thereof (FIG. 9).

When implementing the invention, the number of the groups of furnace tubes relates to the capability of the furnace, and it can be determined in accordance with the design conditions of the feed stocks, the yield of the cracking furnace, the runlength, etc.

The process performance parameters of different embodiments adopting 48 radiant coils are as following:

Comparative Embodiment

Even Diameter

TABLE 1

| structural parameters (even diameter) | | | | |
|---|---|---|---|---|
| | First pass | Connection member | Second pass | Total |
| Number of the tubes | 48 | 48 | 48 | |
| Inner diameter of tubes: m | 0.05707 | 0.05707 | 0.05707 | |

TABLE 1-continued

| structural parameters (even diameter) | | | | |
|---|---|---|---|---|
| | First pass | Connection member | Second pass | Total |
| Outer diameter of tubes: m | 0.0707 | 0.0707 | 0.0707 | |
| Length of the tubes: m | 11.6185 | 2.6885 | 11.6185 | 25.9255 |

Embodiment 1

Once Diameter-Varying

TABLE 2

| structural parameters (once diameter-varying) | | | | |
|---|---|---|---|---|
| | First pass | Connection member | Upper portion of second pass | Total |
| Number of the tubes | 48 | 48 | 48 | |
| Inner diameter of tubes: m | 0.0510 | 0.0510 | 0.0635 | |
| Outer diameter of tubes: m | 0.0646 | 0.0646 | 0.0771 | |
| Length of the tube: m | 11.6185 | 2.6885 | 11.6185 | 25.9255 |

Embodiment 2

Twice Diameter-Varying

TABLE 3

| structural parameters (twice diameter-varying) | | | | |
|---|---|---|---|---|
| | Upper portion of First pass | Lower portion of first pass, connection member, lower portion of second pass | Upper portion of second pass | Total |
| Number of the tubes | 48 | 48 | 48 | |
| Inner diameter of tube: m | 0.0510 | 0.05577 | 0.0635 | |
| Outer diameter of tube: m | 0.0646 | 0.0694 | 0.0811 | |
| Length of the tube: m | 8.6010 | 8.4415 | 8.8830 | 25.9255 |

Embodiment 3

Triple Diameter-Varying

TABLE 4

| structural parameters (triple diameter-varying) | | | | | |
|---|---|---|---|---|---|
| | Upper portion of First pass | Lower portion of first pass, connection member | Lower portion of second pass | Upper portion of second pass | Total |
| Number of the tubes | 48 | 48 | 48 | 48 | |
| Inner diameter of tube: m | 0.0510 | 0.0540 | 0.0580 | 0.0641 | |
| Outer diameter of tube: m | 0.0646 | 0.0676 | 0.0716 | 0.0817 | |
| Length of the tube: m | 7.5000 | 6.8070 | 5.9600 | 5.6585 | 25.9255 |

Figure 10:
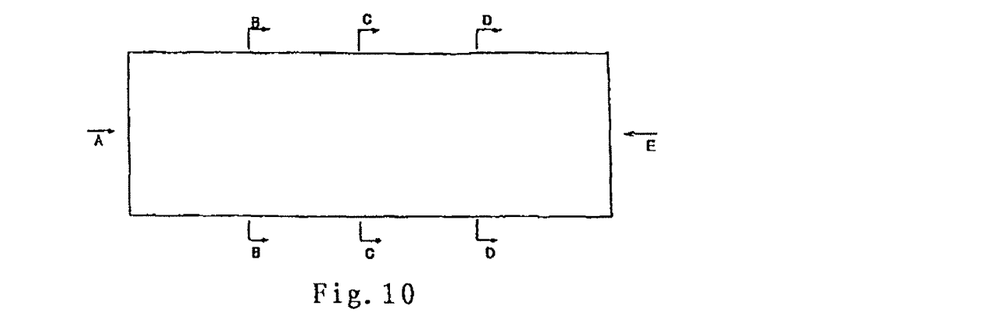
FIG. 10 is a schematic side view showing a tube section with a twisted baffle in accordance with an embodiment of the present invention, wherein the cross sectional positions B-B, C-C and D-D are shown.
Figure 11:
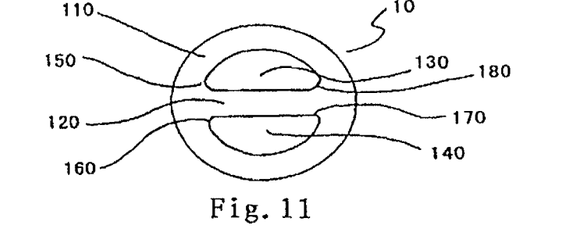
FIG. 11 is a schematic end view seeing according to arrow A or arrow E of FIG. 10.

In addition, as shown in FIGS. 10-14, the present invention also provides a tube section 100 with twisted baffle. From the sectional view shown in FIG. 11, it can be seen that the tube section 100 with a twisted baffle according to the present invention comprises a tube or flue portion 110 and a twisted baffle or turbulator portion 120. Said twisted baffle portion 120 is integrated with said tube portion 110 of the tube section 100. As shown in FIG. 11, said twisted baffle portion 120 extends diametrically across said tube portion 110 so as to divide the inner cavity of the tube section 100 into a pair of passages 130 and 140 for flowing in-process materials. Said passages 130 and 140 have substantially the same cross section area.

According to the concept of the present invention, in every cross section of said tube section 100, each of the transition zones between the surface of said twisted baffle and the inner wall surface of said tube section 100 in the passages 130 and 140, i.e., the corner portions 150, 160, 170 and 180 as shown in FIG. 11, are in the shape of a concave circular arc. Specifically, the radius of said concave circular arc cannot be too long, otherwise, the passages 130 and 140 will be too narrow so as to limit the flow rate of the in-process materials. On the other hand, the radius of said concave circular arc cannot be too short, otherwise, the in-process materials will form eddy and be easy to begin coking in the corner portions.

The length of the tube section with twisted baffle as shown in FIG. 10 is one pitch. Therefore, the end view seen in the direction of arrow A is the same as that seen in the direction of arrow E. As shown in FIG. 11, the twisted baffle portion 120 is in the horizontal state.

Figure 12:
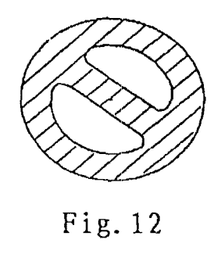
FIG. 12 is a cross sectional view taken along line B-B of FIG. 10.

FIG. 12 shows a sectional view of the tube section 100 of FIG. 10, which is located in the point of ¼ of the entire length of the tube section 100 from the left end thereof. As shown in FIG. 12, the twisted baffle 120 is in an inclined state with an angle of 45° of inclination leftward and upward.

Figure 13:
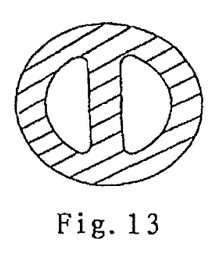
FIG. 13 is a cross sectional view taken along line C-C of FIG. 10.

FIG. 13 shows a sectional view of the tube section 100 of FIG. 10, which is located in the point of ½ of the entire length of the tube section 100 from the left end thereof. As shown in FIG. 13, the twisted baffle 120 is in a vertical state.

Figure 14:
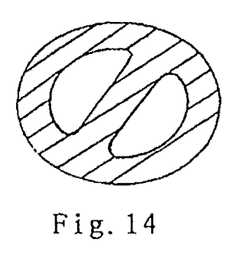
FIG. 14 is a cross sectional view taken along line D-D of FIG. 10.

FIG. 14 shows a sectional view of the tube section 100 of FIG. 10, which is located in the point of ¾ of the entire length of the tube section 100 from the left end thereof. As shown in FIG. 14, the twisted baffle 120 is in an inclined state with an angle of 45° of inclination rightward and upward.

In a word, in the present invention, the geometrical form and dimensions in every axially cross sections of the tube section 100 are always the same, the difference is only in that the twisted baffle portion 120 is in different angles of inclination. The tridimensional shape of the twisted baffle portion 120 can be figured out with FIGS. 10 to 14.

In practice, the twisted baffle portion 120 can be twisted both in the left-handed way and in the right-handed way.

The twisted baffle portion 120 can be arranged diametrically or not diametrically (offset from the diameter direction). When arranged not diametrically, the passages 130 and 140 would have different cross-sectional areas.

The cross section of the twisted baffle portion 120 can be linear (as shown in FIGS. 10-14), or can be curvilinear (not shown).

According to practical requirements, the twisted baffle portion 120 can be designed to have a more complex form so as to divide the inner cavity of the tube section into more than two passages for flowing in-process materials.

In the present invention, the term "pitch" S refers to an axial length of the tube section with every twisted angle 180° of the twisted baffle. The term "twisted ratio" Y refers to the ratio between the pitch S and the internal diameter D of said tube section, i.e., $Y=S/D$.

Accordingly, when the value of Y is smaller, the twisted degree of the twisted baffle is higher. Therefore, the in-process materials in the tube section have a higher tendency of lateral flowing, the heat transfer efficiency is better, and the coking tendency would be better decreased. However, if the value of Y is too small, the resistance to the flowing in-process materials would be greatly increased and thus the flowing speed of the in-process materials would be limited.

On the other hand, when the value of Y is larger, the twisted degree of the twisted baffle is lower. Therefore, the in-process materials in the tube section have a lower tendency of lateral flowing, the resistance to the flowing in-process materials would be decreased and thus the flowing speed of the in-process materials would be improved. However, the heat transfer efficiency would be decreased, and the coking tendency would be less decreased.

Therefore, it is important to determine a suitable twisted ratio. In the present invention, $Y=2.5$ can realize perfect nice effect; while the apparatus would work very well when Y is selected from the range of from 2 to 3.

If the tube section with twisted baffle is axially provided in the entire length of the furnace tubes, the efficiency of the heat transfer can be greatly increased. However, the resistance to the flowing in-process materials would also be increased greatly and therefore the flowing speed would be decreased. For this reason, in the present invention, the tube section with twisted baffle is only arranged at several places of the furnace tubes, and two adjacent tube sections with twisted baffle are separated from each other by a certain length of the tube without twisted baffle (empty tube section). As the in-process materials has a helical inertia force when leaving the tube section with twisted baffle, the in-process materials can still flow forwardly while move helically within the empty tube section.

The interval between two adjacent tube sections with twisted baffle can be set at least 5 pitches. In accordance with several preferred embodiments, the interval can be 15 to 20 pitches.

TABLE 5 comparison of comparative example and the embodiments

| | | Comparative example | | Embodiment 1 | | Embodiment 2 | | Embodiment 3 | |
|---|---|---|---|---|---|---|---|---|---|
| | | Without twisted baffle | With twisted baffle | Without twisted baffle | With twisted baffle | Without twisted baffle | With twisted baffle | Without twisted baffle | With twisted baffle |
| Incoming hydrocarbon amount | kg/h. per furnace | 30000.00 | 30000.00 | 30000.00 | 30000.00 | 30000.00 | 30000.00 | 30000.00 | 30000.00 |

TABLE 5-continued comparison of comparative example and the embodiments

| | | Comparative example | | Embodiment 1 | | Embodiment 2 | | Embodiment 3 | |
|---|---|---|---|---|---|---|---|---|---|
| | | Without twisted baffle | With twisted baffle | Without twisted baffle | With twisted baffle | Without twisted baffle | With twisted baffle | Without twisted baffle | With twisted baffle |
| Diluting steam | kg/h. per furnace | 15000.00 | 15000.00 | 15000.00 | 15000.00 | 15000.00 | 15000.00 | 15000.00 | 15000.00 |
| Water to oil ratio | Wt ratio | 0.5000 | 0.5000 | 0.5000 | 0.5000 | 0.5000 | 0.5000 | 0.5000 | 0.5000 |
| Inlet temperature of radiation section | °C. | 620.00 | 620.00 | 620.00 | 620.00 | 620.00 | 620.00 | 620.00 | 620.00 |
| Outlet temperature of radiation section | °C. | 840 | 840 | 840 | 840 | 840 | 840 | 840 | 840 |
| Inlet pressure of radiation section | MPa(G) | 0.1753 | 0.1885 | 0.1634 | 0.175 | 0.1566 | 0.1673 | 0.1523 | 0.1622 |
| Outlet pressure of radiation section | MPa(G) | 0.1084 | 0.1085 | 0.1062 | 0.1063 | 0.105 | 0.105 | 0.1043 | 0.1044 |
| Total pressure drop of radiation section | MPa | 0.0669 | 0.0800 | 0.0572 | 0.0687 | 0.0516 | 0.0623 | 0.048 | 0.0578 |
| Average resident time at inlet and outlet | Sec | 0.2023 | 0.2045 | 0.2144 | 0.2166 | 0.2234 | 0.2256 | 0.2302 | 0.2323 |
| Average thermal strength of tubes | $GJ/m^2 \cdot h$ | 0.311 | 0.3118 | 0.3035 | 0.304 | 0.2987 | 0.2992 | 0.2952 | 0.2957 |
| Ethylene yield | wt % | 28.83 | 28.96 | 29.27 | 29.39 | 29.57 | 29.7 | 29.77 | 29.89 |
| Propylene yield | wt % | 15.2 | 15.17 | 15.09 | 15.06 | 15 | 14.95 | 14.92 | 14.87 |
| Butadiene yield | wt % | 5.85 | 5.84 | 5.83 | 5.83 | 5.81 | 5.8 | 5.8 | 5.79 |
| Total yield | wt % | 49.88 | 49.97 | 50.19 | 50.28 | 50.38 | 50.45 | 50.49 | 50.55 |
| runlength | Day | 69 | 77 | 70 | 78 | 71 | 80 | 72 | 82 |

When viewing table 5, it can be seen that:

When the twisted baffle is added, the respective properties are better, except that the pressure drop increases a bit.

The more frequent the diameter-varying, the better the properties.

The invention claimed is:

1. An ethylene cracking furnace comprising a high pressure steam drum, a convection section, a radiant section, multiple groups of radiant coils arranged vertically in the firebox of the radiation section, burners and transfer line exchangers, each radiant coil comprising a first-pass tube, a second-pass tube and a connection member for connecting the first-pass tube and the second-pass tube; feedstocks being introduced into an inlet end of the first-pass tube and outflow from an outlet end of the second-pass tube; characterized in that:

said first-pass tube and said second-pass tube are non-split radiant tubes, and the centerlines of the respective furnace tubes are within a common plane;

said connection member is a tridimensional structural member comprising an inlet bending tube, a return bending tube and an outlet bending tube; each first-pass tube is connected to an end of an inlet bending tube at the bottom end of the first-pass tube distal to the inlet end thereof, another end of the inlet bending tube is connected to an end of a return bending tube, another end of the return bending tube is connected to an end of an outlet bending tube, and another end of the outlet bending tube is connected to the bottom end of a second-pass tube that is distal to the outlet end thereof;

said inlet bending tubes and said outlet bending tubes are arranged at two sides of the plane containing the centerlines of said first-pass tubes and said second-pass tubes, respectively; a plane formed by the centerlines of a group of inlet bending tubes intersects with a plane formed by the centerlines of a group of outlet bending tubes, the intersecting line is within the plane containing the centerlines of said first-pass tubes and said second-pass tubes, and said two planes formed by the centerlines of the inlet bending tubes and the outlet bending tubes are symmetrical with respect to the plane containing the centerlines of said first-pass tubes and said second-pass tubes; the return bending tubes connecting the group of inlet bending tubes and the group of outlet bending tubes are parallel to each other, and their projections in a top view are straight lines with the same length; the projections of the respective connection members in a side view are the same curve line that is symmetrical, continuous and closed, and the inner diameters of said radiant coils are selected from a group consisting of:

(1) the inner diameter of said first-pass tube equals to the inner diameter of said connection member, the inner diameter of said second-pass tube differs from the inner diameter of said first-pass tube and said connection member, the inner diameter of said second-pass tube is larger than inner diameter of said first-pass tube and said connection member;

(2) the inner diameter of said first-pass tube equals to the inner diameter of said connection member, the inner diameter of the lower portion of said second-pass tube equals to the inner diameter of said first-pass tube and said connection member, the inner diameter of the upper portion of said second-pass tube is larger than the inner diameter of the lower portion thereof;

(3) the inner diameter of said first-pass tube is even, the inner diameter of said connection member is larger than the inner diameter of said first-pass tube, the inner diameter of said second-pass tube equals to the inner diameter of said connection member;

(4) the inner diameter of said first-pass tube is even, the inner diameter of said connection member is larger than the inner diameter of said first-pass tube, the inner diameter of the lower portion of said second-pass tube equals to the inner diameter of said connection member, the inner diameter of the upper portion of said second-pass tube is larger than the inner diameter of the lower portion thereof;

(5) the inner diameter of said first-pass tube is even, the inner diameter of said connection member is larger than the inner diameter of said first-pass tube, the inner diameter of the lower portion of said second-pass tube is larger than the inner diameter of said connection member, the inner diameter of the upper portion of said second-pass tube is larger than the inner diameter of the lower portion thereof; and (6) the inner diameter of said first-pass tube is variational: the inner diameter of the lower portion of said first-pass tube is larger than the inner diameter of the upper portion thereof.

2. An ethylene cracking furnace according to claim 1, wherein, in each group of radiant coils, the respective first-pass tubes are parallel to each other, the respective second-pass tubes are parallel to each other, and the first-pass tubes and the second-pass tubes are parallel to each other; the projection of the plane containing the centerlines of said first-pass tubes and said second-pass tubes in a top view is a straight line; said respective inlet bending tubes are parallel to each other with their projections in a top view forming the same inlet angle with respect to said straight line; said respective outlet bending tubes are parallel to each other with their projections in a top view forming the same outlet angle with respect to said straight line; said inlet angle equals to said outlet angle.

3. An ethylene cracking furnace according to claim 1, wherein, in each group of radiant coils, the respective first-pass tubes are parallel to each other, the respective second-pass tubes are parallel to each other, and the first-pass tubes and the second-pass tubes are parallel to each other; the projection of the plane containing the centerlines of said first-pass tubes and said second-pass tubes in a top view is a straight line; said respective inlet bending tubes are not parallel to each other with their projections in a top view forming different inlet angles with respect to said straight line; said respective outlet bending tubes are not parallel to each other with their projections in a top view forming different outlet angles with respect to said straight line; but for each radiant tube, said inlet angle equals to said outlet angle.

4. An ethylene cracking furnace according to any one of claims 1 to 3, wherein said radiant coils comprise at least one tube section having a twisted baffle therein, said twisted baffle extends inside the tube section along the axis thereof to form two helical passages at the opposite sides of said twisted baffle, said twisted baffle being integrally formed with said tube section.

5. An ethylene cracking furnace according to claim 4, wherein the twisted angle of said twisted baffle is between 100~360°, the axial length of said tube section with every twisted angle 180° of the twisted baffle is a pitch, the ratio of said pitch to the inner diameter of said tube section is in the range of from 2 to 3; the thickness of said twisted baffle substantially corresponds to that of the wall of said tube section; in each cross-section of said tube section, the transition section from the surface of said twisted baffle to the surface of said tube section, and vice versa, is in the shape of a concave circular arc.

6. An ethylene cracking furnace according to claim 5, wherein said radiant coils comprise multiple tube sections each having a twisted baffle therein, the multiple tube sections are arranged in at least a predetermined length of said radiant coils spaced apart with each other, the distance between two adjacent tube sections is at least five pitches.

7. An ethylene cracking furnace according to claim 1, wherein the projection shape of said return bending tube in a side view is camber, semi-circular, semi-ellipse or parabola.

8. An ethylene cracking furnace according to claim 1, wherein said group of radiant coils comprises at least two radiant coils, and all of the first-pass tubes and all of the second-pass tubes in each group of radiant coils are collectively arranged, respectively.

9. An ethylene cracking furnace according to claim 1, wherein the second-pass tubes of two groups of radiant coils are adjacently arranged so as to form a module; a plurality of said modules are arranged within the firebox of the cracking furnace, and the centerlines of the first-pass tubes and the second-pass tubes of each of the groups are within the same plane.

10. An ethylene cracking furnace according to claim 1, wherein, multiple groups of radiant coils is arranged in the firebox of the cracking furnace, the first-pass tube of one group of radiant coils are arranged adjacent to the second-pass tube of another group of radiant coils, and the centerlines of the first-pass tubes and the second-pass tubes of each of the groups are within the same plane.

* * * * *